(12) United States Patent
Brennan

(10) Patent No.: US 6,921,636 B1
(45) Date of Patent: *Jul. 26, 2005

(54) METHOD AND APPARATUS FOR CONDUCTING AN ARRAY OF CHEMICAL REACTIONS ON A SUPPORT SURFACE

(75) Inventor: Thomas M. Brennan, San Francisco, CA (US)

(73) Assignee: Metrigen, Inc., Burlingame, CA (US)

( * ) Notice: Subject to any disclaimer, the term of this patent is extended or adjusted under 35 U.S.C. 154(b) by 257 days.

This patent is subject to a terminal disclaimer.

(21) Appl. No.: 09/715,426

(22) Filed: Nov. 16, 2000

Related U.S. Application Data

(63) Continuation of application No. 09/314,456, filed on May 18, 1999, now Pat. No. 6,210,894, which is a continuation of application No. 08/465,761, filed on Jun. 6, 1995, now Pat. No. 5,985,551, which is a continuation of application No. 08/068,540, filed on May 27, 1993, now Pat. No. 5,474,796, which is a continuation-in-part of application No. 07/754,614, filed on Sep. 4, 1991, now abandoned.

(51) Int. Cl.[7] .......................... C12Q 1/68; C12P 19/34; C07K 16/00
(52) U.S. Cl. ...................... 435/6; 435/91.2; 435/283.1; 435/285.1; 422/57; 422/58; 530/334; 530/335; 530/336
(58) Field of Search ........................ 435/6, 91.2, 283.1, 435/285.1; 422/57, 58; 536/334, 335, 336

(56) References Cited

U.S. PATENT DOCUMENTS

| | | | |
|---|---|---|---|
| 3,736,042 A | | 5/1973 | Markozits et al. |
| 4,705,705 A | | 11/1987 | Bross |
| 5,063,081 A | | 11/1991 | Cozzette et al. |
| 5,143,854 A | * | 9/1992 | Pirrung et al. ............... 436/518 |
| 5,252,743 A | | 10/1993 | Barrett et al. |
| 5,412,087 A | | 5/1995 | McGall et al. |
| 5,424,186 A | | 6/1995 | Fodor et al. |
| 5,445,934 A | | 8/1995 | Fodor et al. |
| 5,449,754 A | | 9/1995 | Nishioka |
| 5,474,796 A | | 12/1995 | Brennan |
| 5,510,270 A | | 4/1996 | Fodor et al. |
| 5,700,637 A | | 12/1997 | Southern |
| 5,744,305 A | | 4/1998 | Fodor et al. |
| 5,985,551 A | * | 11/1999 | Brennan ........................ 435/6 |
| 6,054,270 A | | 4/2000 | Southern |

FOREIGN PATENT DOCUMENTS

| | | |
|---|---|---|
| EP | 0 161 058 A1 | 11/1985 |
| EP | 373203 | 8/1994 |
| WO | WO 89/19866 | 11/1989 |
| WO | WO 90/03382 | 4/1990 |
| WO | WO 90/15070 | 12/1990 |

OTHER PUBLICATIONS

Fodor et al, "Light–directed spatially addressable parallel chemical synthesis", (Feb. 1991) 251:767–773.*
Fodor, et al., Light–Directed, Spatially Addressable Parallel chemical Synthesis, *Science* 251:767–773 (1991).
Ramirez, Levy, Ringold, Rosenkranz, Wiley, Esterie, Bailey, and Mintha *J. Organic chemistry* 21:1333–1335 (1956).
Khrapko, et al. An Oligonucleotide by Hybridization Approach to DNA Sequencing, *FEBS Letters* 256:118–122 (1989).
Drmanac, et al., Sequencing of Megabase Plus DNA by Hybridization Theory of the Method, *Genomic* 4:114–128 (1989).
Geysen, et al., Strategies for Epitope Analysis Using Peptide Synthesis, *J. Immunol. Methods* 102:259–274 (1987).
Southern and Maskos, Support–bound Oligonucleotides, *Chem Abst.,*—Abstract No. 152979r, 113:152984 (1990).
Mandenius, et al., Reversible and Specific Interaction of Dehydrogenases with a Coenzyme–Coated Surface Continuously Monitored with a Reflectometer, *Anal. Biochem.* 157:283–288 (1986).
Southern and Maskos, Analysing Nucleic Acids by Hybridisationof Oligonucleotides: Analysis of Mutations, Abstracts of papers presented at the 1991 meeting fo Genome Happing and Sequencing, Cold Spring Harbor Laboratory, Cold Spring Harbor, N.Y. (1991).
Froehler, et al., Synthesis of DNA via Deoxynucleoside H–phosphonate Intermediates, *Nuc. Acids Res.* 14:5399–5407 (1986).
Kyser, et al., Design of an Impulse Ink Jet, *J. Applied Photographic Engineering* 7: 73–79 (1981).
Drmanac, et al., Reliable Hybridization of Oligonucleotides as Short as Six Nucleotides, *DNA an Cell Biology* 9:527–534 (1990).
McGraw, et al., Sequence–Dependent Oligonucleotide–Target Duplex Stabilities: Rules from Empirical Studes with a Set of Twenty–Mers, *Biotechniques* 8:674–678 (1990).
Wood, et al., Base Composition–Independent Hybridization in Tetramethylammonium Chloride: A Method for Oligonucleotide Screening of Highly Complex Gene Libraries, *PNAS USA* 82:1585–1588 (1985).

* cited by examiner

Primary Examiner—Jeffrey Fredman
(74) Attorney, Agent, or Firm—Albert P. Halluin; Maya Skubatch; Wilson Sonsini Goodrich & Rosati, LLC

(57) ABSTRACT

The invention provides apparatus and methods for determining the nucleotide sequence of target nucleic acids using hybridization to arrays of oligonucleotides. The invention further provides apparatus and methods for identifying the amino acid sequence of peptides that bind to biologically active macromolecules, by specifically binding biologically active macromolecules to arrays of peptides or peptide mimetics.

9 Claims, 7 Drawing Sheets

| A | C | |
|---|---|---|
| G | T | Matrix |

| | | | | | | | |
|---|---|---|---|---|---|---|---|
| AAA | AAC | ACA | ACC | CAA | CAC | CCA | CCC |
| AAG | AAT | ACG | ACT | CAG | CAT | CCG | CCT |
| AGA | AGC | ATA | ATC | CGA | CGC | CTA | CTC |
| AGG | AGT | ATG | ATT | CGG | CGT | CTG | CTT |
| GAA | GAC | GCA | GCC | TAA | TAC | TCA | TCC |
| GAG | GAT | GCG | GCT | TAG | TAT | TCG | TCT |
| GGA | GGC | GTA | GTC | TGA | TGC | TTA | TTC |
| GGG | GGT | GTG | GTT | TGG | TGT | TTG | TTT |

DNA Fragment

-----ATTCTTGTTA---

```
ATT
 TTC                    TTA, TTG
  TCT
   CTT
    TTG                 TTA
     TGT
      GTT
       TTA
```

Correct Assembly      Possible N+1 List

Fig 1

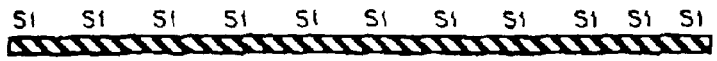
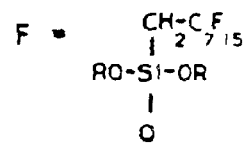
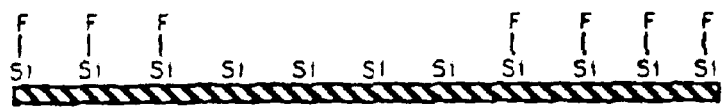
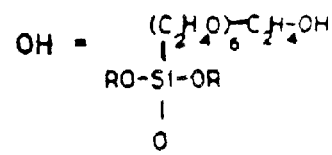
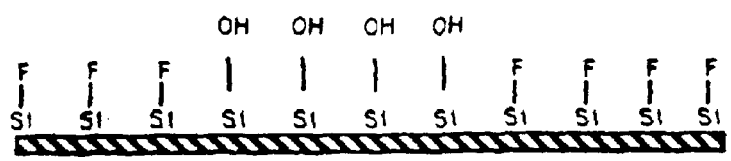
Fig. 2

SEQUENCE LISTING

<160> NUMBER OF SEQ ID NOS: 2

<210> SEQ ID NO 1
<211> LENGTH: 192
<212> TYPE: DNA
<213> ORGANISM: Artificial Sequence
<220> FEATURE:
<223> OTHER INFORMATION: Trimer matrix

<400> SEQUENCE: 1

```
aaaaacacaa cccaacaccc acccaagaat acgactcagc atccgcctag aagcataatc        60
cgacgcctac tcaggagtat gattcggcgt ctgcttgaag acgcagccta atactcatcc       120
gaggatgcgg cttagtattc gtctggaggc gtagtctgat gcttattcgg gggtgtggtt       180
tggtgtttgt tt                                                            192
```

<210> SEQ ID NO 2
<211> LENGTH: 10
<212> TYPE: DNA
<213> ORGANISM: Artificial Sequence
<220> FEATURE:
<223> OTHER INFORMATION: DNA fragment

<400> SEQUENCE: 2

```
attcttgtta                                                               10
```

METHOD AND APPARATUS FOR CONDUCTING AN ARRAY OF CHEMICAL REACTIONS ON A SUPPORT SURFACE

This is a continuation of U.S. patent application Ser. No. 09/314,456, filed May 18, 1999 now U.S. Pat. No. 6,210,894, which is a continuation of U.S. patent application Ser. No. 08/465,761, filed Jun. 6, 1995 (Now U.S. Pat. No. 5,985,551), which is a continuation of U.S. patent application Ser. No. 08/068,540, filed May 27, 1993 (now U.S. Pat. No. 5,474,796), which is a continuation-in-part of U.S. patent application Ser. No. 07/754,614, filed Sep. 4, 1991, abandoned.

BACKGROUND OF THE INVENTION

1. Field of the Invention

The invention relates to methods for determining nucleic acid sequences or peptide sequences that bind biologically active macromolecules. More particularly, the invention relates to the use of hybridization to oligonucleotide arrays to determine nucleic acid sequences or binding to peptide arrays to determine amino acid sequences involved in peptide binding.

2. Summary of the Related Art

The determination of the nucleotide sequence of nucleic acids and the amino acid sequence of peptides and proteins is central to many critical analyses in molecular biology. Such sequence determination allows investigation of mutations that are responsible for inherited diseases and neoplastic conditions. These determinations potentially allow comparison of genetic alleles responsible for variation in human inherited traits. Finally, such determination allow identification of the precise nature of molecular interactions necessary for a plethora of critical biological or biochemical functions. These promises have led to proposals for ambitious projects involving macromolecule sequence determination, such as the proposed sequencing of the entire human genome. Consequently, procedures for sequencing nucleic acids and peptides have developed rapidly and become well known in the art. Nevertheless, existing procedures for sequence determination are sufficiently time consuming to limit the speed at which ambitious sequencing projects can proceed. This state of affairs has led to proposals for newer, nonconventional sequencing procedures that are more rapid than existing techniques. One promising idea is to utilize hybridization to determine nucleotide sequences.

Proposals for the direct sequencing of DNA by hybridization with arrays of oligonucleotides are known in the art. Drmanac et al., Genomics 4: 114 (1989) proposes hybridization array-mediated DNA sequencing by binding target DNA to a dot blot membrane, followed by probing with an array of oligonucleotides. Khrapko et al., FEBS Letters 256: 118 (1989) proposes hybridization array-mediated DNA sequencing by binding the oligonucleotide array to a support membrane, followed by probing with target DNA.

Synthesis of arrays of bound oligonucleotides or peptides is also known in the art. Houghton, in the Multiple Peptide System product brochure describes the T-bag method, in which an array of beads is physically sorted after each interaction. This method becomes unwieldy for the preparation of large arrays of oligonucleotides. Geysen et al., J. Immunol. Methods 102: 259 (1987) discloses the pin method for the preparation of peptide arrays. The density of arrays that may be produced by this method is limited, and the dipping procedure employed in the method is cumbersome in practice. Southern, Genome Mapping and Sequencing Conference, May 1991, Cold Spring Harbor, N.Y., disclosed a scheme for oligonucleotide array synthesis in which selected areas on a glass plate are physically masked and the desired chemical reaction is carried out on the unmasked portion of the plate. In this method it is necessary to remove the old mask and apply a new one after each interaction. Fodor et al., Science 251: 767 (1991) describes a method for synthesizing very dense 50 micron arrays of peptides (and potentially oligonucleotides) using mask-directed photochemical deprotection of synthetic intermediates. This method is limited by the slow rate of photochemical deprotection and by the susceptibility to side reactions (e.g., thymidine dimer formation) in oligonucleotide synthesis. Khrapko et al., FEBS Letters 256: 118 (1989) suggests simplified synthesis and immobilization of multiple oligonucleotides by direct synthesis on a two dimensional support, using a printer-like device capable of sampling each of the four nucleotides into given dots on the matrix. However, no particulars about how to make or use such a device are provided.

Some methods for permanently attaching oligonucleotides to glass plates in a manner suitable for oligonucleotide synthesis are known in the art. Southern, Chem. Abst. 113: 152979r (1990) describes a stable phosphate ester linkage for permanent attachment of oligonucleotides to a glass surface. Mandenius et al., Anal. Biochem. 157: 283 (1986) teaches that the hydroxyalkyl group resembles the 5'-hydroxyl of oligonucleotides and provides a stable anchor on which to initiate solid phase synthesis.

A variety of procedures for synthesis of oligonucleotides are, of course, known in the art. Matteucci et al., Nuc. Acids Res. 14: 5399 (1986) discloses an H-phosphonate protocol that uses excess pivaloyl chloride/pyridine for activation, thereby providing a self-capping coupling step.

Special apparatus is required to deliver minute quantities of materials precisely for the preparation of oligonucleotide arrays. Some information about piezoelectric pumps is known in the photographic art. Kyser et al., J. Applied Photographic Engineering 7: 73 (1981) teaches that energizing a piezoelectric element deforms the cavity much like a one-sided bellows. Parameters for oligonucleotide hybridization also are known in the art. Drmanac et al., DNA and Cell Biology 2: 527 (1990) teaches that maximum selectivity in hybrid formation occurs near the $T_{m1/2}$ of an 8-mer, or about 25° C., and that selectivity decreases at higher temperatures. McGraw et al., BioTechniques 8: 674 (1990) teaches that the bond energy of a GC pair is nearly twice that of an AT pair in low ionic strength SSC buffers. Wood et al., Proc. Natl. Acad. Sci. USA 82: 1585 (1985) teaches that 3 M trimethylammonium chloride stabilizes the AT base pair sufficiently to make the $T_{m1/2}$ of a hybrid independent of base composition, and dependent only on the number of mismatches.

In summary, the related art contains numerous ideas and information related to the synthesis of arrays of oligonucleotides or peptides for the determination of nucleotide sequences or the amino acid sequences of specific binding peptides. However, existing or suggested methods are limited, and do not conveniently and reliably produce the very large, high density arrays necessary for effective large-scale sequencing. There is, therefore, a need for new methods for preparing large high density arrays of oligonucleotides or peptides for sequencing based upon oligonucleotide hybridization or peptide binding Ideally, such methods should utilize relatively simple machinery to produce large, dense arrays of solid phase bound oligonucleotides or peptides in a reproducible and rapid manner.

BRIEF SUMMARY OF THE INVENTION

The invention provides a method for producing very large, high density arrays of oligonucleotides for use in hybridization sequencing. According to the method of the invention, these arrays of oligonucleotides are synthesized by massively parallel chemical reactions on glass plates. Each element in the array is separated from its nearest neighbors by a surface tension wall. For each element, stable hydroxyalkyl groups are bound to the plate and act as 5'-hydroxyl surrogates on which to initiate strand synthesis. Synthetic reactions are carried out on a picoliter scale, with specific nucleotides delivered to each element by arrays of piezoelectric pumps. The use of the hydroxyalkyl linker arm enables removal of purine and pyrimidine blocking groups without cleavage of the oligonucleotide from the support.

The invention further provides oligonucleotide array plates produced according to this method of the invention. In preferred embodiments, the invention provides array plates having at least 1024×1024 distinct and separately bound oligonucleotide elements, each element containing at least 0.1 femtomoles of oligonucleotide for a total of greater than $10^6$ distinct oligonucleotide elements, each element separated by virtue of a surface tension wall.

The invention also provides a method for determining the nucleotide sequence of a target nucleic acid. The target nucleic acid is labelled by conventional methods and hybridized to an array plate according to the invention. The array plate having bound labelled target nucleic acid is then washed at appropriate stringency and the presence and location of bound labelled target nucleic acid is determined using scanning analyzers. Since the sequence of the covalently attached oligonucleotide in each element on the array is known, this allows the unambiguous determination of the nucleotide sequence of the target nucleic acid.

Each aspect of the invention discussed above relates to determining the nucleotide sequence of target nucleic acids. However, the methods of the invention may also be applied to the determination of peptides or peptide mimetics that bind biologically active receptors. In this aspect, peptide arrays of known sequence can be applied to glass plates using the same piezoelectric pump/surface tension wall method described for oligonucleotide array plate construction. The resulting array of peptides can then be used in binding analyses with biologically active receptor ligands to screen for peptide mimetics of receptor agonists and antagonist. Thus the invention provides a method for producing peptide array plates, peptide array plates having covalently bound peptides separated by surface tension wells, and methods of using such peptide array plates to screen for peptide mimetics of receptor agonists and antagonists.

BRIEF DESCRIPTION OF THE DRAWINGS

FIG. 1: Hybridization analysis using arrays of trimers. Individual dots that have bound the DNA fragment are underlined.

FIG. 2: Creation of an array surface that is ready for solid phase oligonucleotide or peptide synthesis.

DETAILED DESCRIPTION OF THE SPECIFIC EMBODIMENTS

Figure 3:
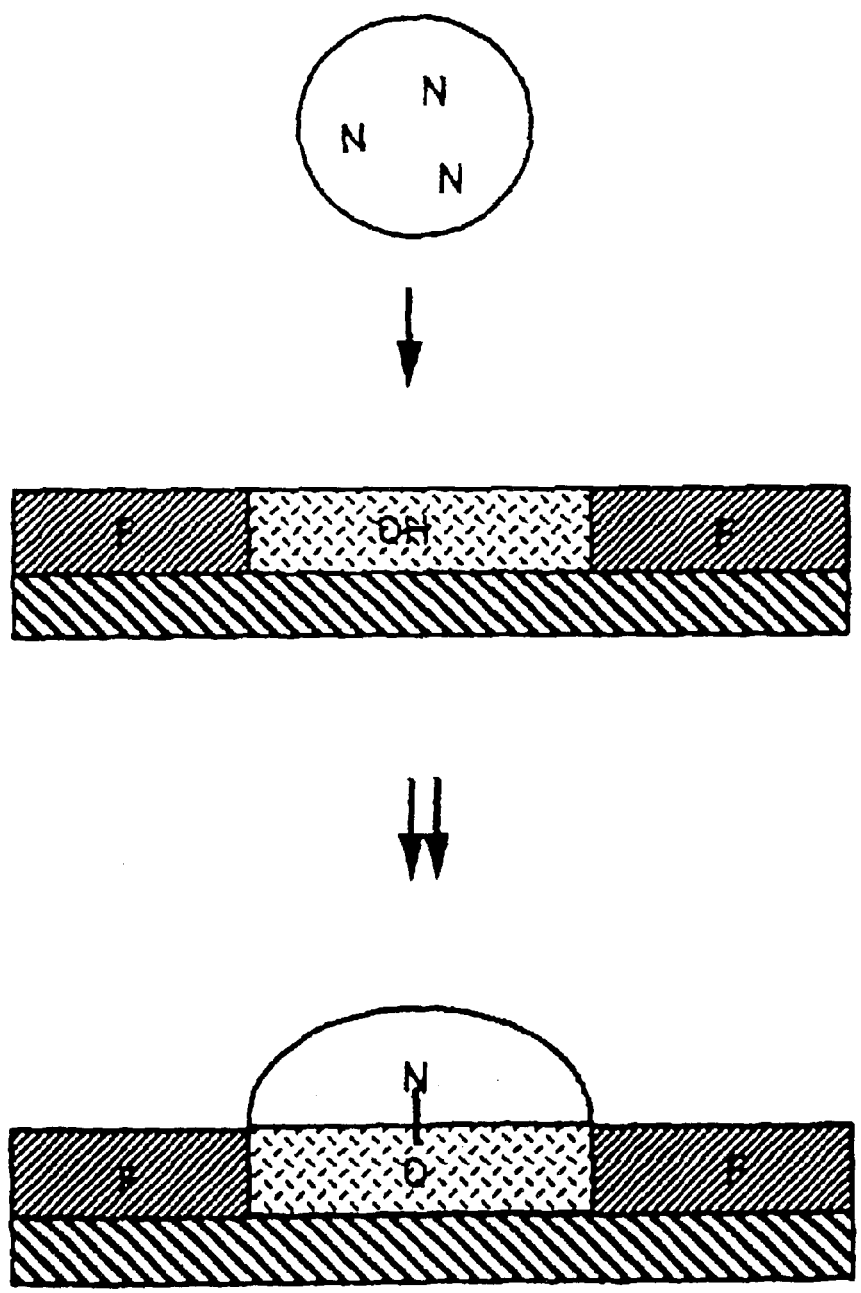
FIG. 3: Surface tension wall effect at the dot-interstice interface. The droplet containing solid phase synthesis reagents does not spread beyond the perimeter of the dot due to the surface tension wall.

The invention relates to the determination of the nucleotide sequence of a nucleic acid using hybridization of the nucleic acid in a labelled form to an array of oligonucleotide elements. The invention also relates to the identification of peptides or peptide mimetics that are capable of binding with high affinity to biologically active macromolecules, using specific binding of the biologically active macromolecules to an array of peptides or peptide mimetics.

In a first aspect, the invention provides a method to directly sequence DNA by hybridization to an array of oligonucleotides. There are $4^N$ possible unique sequences that can be generated in oligonucleotides of length N. When an unknown nucleic acid of length L is probed with a set of all possible oligomers of length N under sufficiently high stringency conditions, hybridization occurs only to that subset of oligonucleotides that contains an exact match to the unknown nucleic acid. As shown in FIG. 1, this subset consists of L overlapping segments, where moving in a 5'-3' direction, successive members differ by the addition of the next 3' residue and deletion of the previous 5' residue.

When a repeat of a particular oligonucleotide sequence is encountered, a branch point in the analysis is created and the order of fragments becomes ambiguous. For random DNA, the average distance between identical repeats, the subfragment length $S_r$ is related to the length of the oligonucleotide probe. On average, slightly less than $3 \times S_f$ of DNA can be ordered per hybridization analysis. The repeat frequency in the mammalian genome is far greater than in random DNA, however, thus potentially limiting applicability of hybridization sequencing, at least where highly repetitive DNA is involved.

Hybridization data from an 11-mer array ($4^{11} = 4 \times 10^6$) of oligonucleotides provides sufficient information to unambiguously order DNA in 1.5 kb segments. The size of the probe library may be reduced by using an array of 11-mers having a full set of 8 internal bases, but having ambiguous bases at the 3' and 5' termini. e.g., [(ATGC)(ATGC)N$_8$ (ATGC)]. By further pruning of selected sequence types, a final library size of 86,000 probes can be used to sequence DNA in 200 bp segments. Application of this approach to a set of overlapping clones allows for megabase sequencing projects, with about 2,100 overlapping clones required to sequence 1 Mbp DNA.

In the method of hybridization sequencing according to the invention, the oligonucleotide array is bound to a support membrane, such as a glass plate. Individual oligonucleotide elements are separated from each other by a surface tension wall. The array is hybridized to labelled target nucleic acid. This approach has the advantages of compact mechanical information processing and minimal variation in the hybridization stringency across a single plate, which provides greater accuracy in the segment analysis.

In the method of hybridization sequencing according to the invention, numerous factors are considered in determining the practical success of hybridization to large arrays for sequencing. The first of these is the optimum length of the hybrid for single base mismatch discrimination. The activation energy for melting or strand separation of DNA is approximately 50 kcal and is nearly independent of length. The rate determining step for hybridization involves the pairing of about 6–8 bases, and longer hybrids do not form any faster than an 8-mer. Maximum selectivity in hybrid formation occurs near the 8-mer $T_{m1/2}$ of about 25° C., and decreases at higher temperatures. However, the stability of the hybrid that is formed, i.e., the melting temperature $T_{m1/2}$ increases with the total number of base pairs in the complex.

A second factor of importance is the ionic composition of the hybridization solution. It is desirable to use conditions under which the melting temperature does not depend on the specific composition of the hybrid. In low ionic strength SSC buffers, the bond energy in a GC pair is nearly twice that of an AT pair. In 3 M Me$_4$NCI, however, the AT pair is sufficiently stabilized that the $T_{m1/2}$ of the hybrid becomes independent of composition and depends only on the number of matches. Over the range of 11–40 bases, the matching selectivity $\Delta T_{m1/2}$ is related to the reciprocal of the total number of base pairs. The use of ambiguous base termini will raise the average $T_{m1/2}$ of a hybrid, but may actually decrease the $\Delta T_{m1/2}$ of a mismatch because of the higher temperature washing step required. An array of exact match 10-mers with a 3 M, Me$_4$NCI wash at 42° C. provides the best compromise between information content and hybridization/washing selectivity.

A third factor is the concentration of the unbound component, i.e., the target nucleic acid. The oligonucleotide loading density in the oligonucleotide element dots preferably does not exceed $3.4 \times 10^{-12}$ moles/cm$^2$. This corresponds to a separation of about 7 nm between adjacent strands, which spacing approximates the average pore size of a 4% T-polyacrylamide gel. This spacing serves to minimize interaction between adjacently bound oligonucleotide-nucleic acid hybrids. One picomole of target nucleic acid in 100 microliters provides a 10 nM solution of the probe. This solution can be spread on a 2.5 cm×2.5 cm surface to a depth of about 160 microns, thus generating a DNA probe target density of $1.6 \times 10^{-13}$ moles/cm$^2$, which is 1/20 that of the bound oligonucleotide density. If only diffusional mixing is provided, hybridization in the exact match regions of the plate quickly slows down as the solution becomes depleted of target nucleic acid. However, within a distance of 5 oligonucleotide element dot diameters, an additional 25 times as much DNA is available. Thus, turbulent mixing over this scale is accomplished using sonic agitation.

Preferred embodiments of the hybridization sequencing method according to the invention are set forth in Example 4. Of course, alternative procedures for labelling of the target nucleic acid can be used, such as the use of different radiolabels (e.g., S$^{35}$), or of photobiotin labelling and fluorescent or chemluminescent detection of hybrids with CCD cameras or epifluorescent microscopes.

In a second aspect, the invention provides a method for identifying the amino acid sequence of peptides capable of binding biologically active macromolecules, such as receptors. Peptides or peptide mimetics that can bind such biologically active macromolecules are good candidates for being agonists or antagonists of the ligands that normally bind the biologically active macromolecules. In this aspect, the invention utilizes essentially the same principles as described for hybridization sequencing of nucleic acids, except that the array element dots are composed of oligopeptides or peptide mimetics, rather than oligonucleotides. Such arrays are synthesized using standard solid phase peptide synthesis procedures. The biologically active macromolecule is then labelled and allowed to bind to the array under standard conditions for receptor-ligand interactions. Since the sequence of each peptide or peptide mimetic is known, the sequence of peptides or peptide mimetics that bind to the biologically active macromolecule is readily determined.

In a third aspect, the invention provides arrays of oligonucleotides, oligopeptides or peptide mimetics; and in a fourth aspect the invention provides a method of making oligonucleotide or peptide array plates. Such arrays are useful for direct nucleic acid sequencing and/or error checking. In addition, they are useful for screening for point or multiple mutation diseases such as sickle cell anemia or cystic fibrosis. Indexed retrievable arrays of pre-made oligonucleotides facilitate the implementation of STS, PCR and primer walking strategies. Arrays of peptides or peptide mimetics are useful in receptor epitope screening and drug design.

Hybridization arrays according to the invention are synthesized on a supporting membrane, preferably on a glass plate. Such synthesis has two principal stages: preparation of an array plate ready for oligonucleotide synthesis, and solid phase synthesis of the oligonucleotides on the array plate. Preparation of an array plate ready for oligonucleotide synthesis involves coating the plate with a substance having a low surface tension, then creating an array of dots of a different material upon the plate surface, the different material having a high surface tension relative to the initial coating material used. The dots are then provided with a covalently attached functional group suitable for the initiation of solid phase oligonucleotide synthesis. Preferred embodiments of this stage of the method according to the invention are illustrated in Example 1. The array plate ready for solid phase synthesis has individual dot elements that are separated from each other by surface tension walls for any solvent that has a surface tension intermediate between that of the dot surface and the interstitial plate surface. In effect the plate becomes an array microtiter dish where the individual wells are defined by surface tension rather than by gravity.

In a preferred embodiment, the array plate comprises a support membrane upon which is situated an array of dots and interstices. The dots have a surface material with a surface tension that is greater than the surface tension of the surface material comprising the interstices. Thus the dots are separated from each other by surface tension wells. In a preferred embodiment the dot surface is hydroxyalkyl siloxane and the interstitial surface is fluoroxysilane. In a preferred embodiment the dots have a diameter of 50 to 100 microns. The dot surfaces are covalently attached to oligonucleotides or to peptides. In a preferred embodiment, a siloxane linkage is provided by a hydroxyalkyl group. In a preferred embodiment the oligonucleotide density is no more than about $3.4 \times 10^{-12}$ moles/cm$^2$, or the spacing between the adjacent oligonucleotide strands is about 6 nm. Most preferably, the oligonucleotides are about 10 nucleotides in length, although shorter or longer oligonucleotides may be used.

Materials other than those described in Example 1 may be used for preparing the array plates. Such materials must be tested for the appropriate qualities. The strength with which an array element binds individual solvent droplets is of primary importance. Surface tension parameters, such as contact angle and solvent wetability can be determined optically. Plates with an array of dots with decreasing diameters and with decreasing separation between targets can be prepared to evaluate the local spreading tendency. The array plates can be examined with a scanning electron microscope to determine the depth of ablation of the first coating in the dot areas. The average surface density of reactive hydroxyls in the target region after photolithography and derivitization, as well as the level of residual hydroxyls in the masked (low surface tension) regions can be evaluated by exhaustive capping with $C^{14}$ acetic anhydride/DMAP in ether to insure good contact with all surfaces. The presence of residual reactive groups in the masked region suggests either incomplete initial derivitization, or the presence of side reactions in the subsequent dot-forming steps. This problem can be remedied by modification of the vigor of the derivatizing conditions.

Maximum volume of the dot areas, without spillage to adjacent regions, is determined both for static and dynamic situations by oc analysis using fluorescent additives in the solvent to detect mixing between adjacent dots. Dot volume can potentially be increased by etching a cavity in the dot area. However, this can potentially cause air bubble trapping, as sharp convex corners in the pumping chamber of capillary electrophoresis picopumps have done.

It is important that droplets do not splatter when they strike the dot surfaces. Droplet behavior on impact can be monitored under a microscope, using a high speed strobe light. Factors influencing splattering are surface tension, viscosity of the liquid, wetness or dryness of the dot surface, and droplet velocity and size. Viscosity can be increased, without adversely affecting nucleotide coupling chemistry, by adding limited amounts of PEG dimethyl ether or DMF.

The second stage of oligonucleotide array plate synthesis is solid phase synthesis of oligonucleotides on the array dots. Any of the standard synthesis protocols, e.g., H-phosphonate, CED phosphoramidite, O-methyl phosphoramidite, may be used. Preferably, the H-phosphonate method is used, since the excess pivaloyl chloride/pyrimidine used for activation in that procedure results in a self-capping coupling step. Thus, there is a lower probability of a partial scrambling due to incomplete reaction at an adjacent dot when the plate is first flooded with acetonitrile to wash off the excess activated nucleotides. In addition, the H-phosphonate method eliminates the aqueous $I_2$ oxidation step of the phosphoramidite methods. Purity is critical, since there is no opportunity to purify the plate-bound oligonucleotides. Preferred embodiments of this stage of the method are set forth in Example 2.

To reduce hybridization interactions between adjacent chains, the loading level in the first cycle can be cut back by reducing the amount of the first nucleotide applied. This requires effective capping of the remaining free hydroxyls in the array dot to preserve high sequence fidelity in the remainder of the synthesis. In the method according to the invention, nucleotides and activators are delivered to the array dots by a picopump head.

A potential problem in the solid phase synthesis stage is misfiring of the head in delivery of the nucleotide or the activator. When a one drop delivery cycle is used for the smaller targets, a second plate-wide capping cycle can be used to insure that improper oligonucleotides are terminated promptly. Oligonucleotides terminated in all but the last cycle are of 8-mer length or less, and are well discriminated against by appropriate stringency in the wash phase. False positives in the hybridization add more ambiguity to the sequence analysis than false negatives.

Nucleotide coupling protocols or plate materials different from those described in Example 2 can be used, subject to testing for efficiency. To evaluate the nucleotide coupling chemistry using a particular protocol, or on a particular plate material, a fusible linker arm is employed for a statistical evaluation of the progress in synthesis of poly T. DMT thymidine 3'-succinate is exhaustively esterified to an entire 64×64 array plate. The total capacity of the array (typically about 1 pmol) is determined by $C^{14}$ acetic anhydride capping. The amount of T esterified to the plate is estimated by the amount of DMT released by DCA deblocking. The array is then subjected to 10 cycles of T coupling and yield is evaluated on the basis of DMT release in each cycle. The completed oligonucleotides are then cleaved from the plate with $NH_4OH$ and the homogeneity of the crude $T_{10}$ product is evaluated by CZE and HPLC. Statistical coupling failures will be represented by the products of less than 10 nucleotide length.

Alternatively, the poly T preparation can be undertaken without using the succinate linker arm. In this case the array is used directly as a 5'-OH, and DMT release serves as the primary monitor for method development. The crude oligo with the hydroxyalkyl link still attached can then be cleaved from the array plate with $BU_4NF$ and analyzed for homogeneity.

In a fifth aspect, the invention provides an apparatus for preparing oligonucleotide or peptide array plates. The apparatus is a picopump which utilizes piezoelectric impulse jets to deliver minute droplets of liquid to a surface in a very precise manner. The piezoelectric pump design is similar to the pumps used in ink jet printing. The picopump is capable of producing 50 micron or 65 picoliter droplets at up to 3000 Hz and can accurately hit a 250 micron target in a 900° C. oven at a distance of 2 cm in a draft free environment. Preferred embodiments of the apparatus according to the invention are set forth in Example 4, and utilize stationary pump heads. Alternatively, disposable moving belt targets can be used. In this embodiment the arrays are laid down continuously and then drawn through successive washing and common chemistry baths. Operating at 1,000 Hz in a continuous synthesis mode, this embodiment can produce $3.6 \times 10^6$ oligonucleotides per nozzle lane per hour.

Alternative pump designs should take into account the following physical and mechanical considerations for reliable performance to be obtained. When a non-compressible fluid inside of a pumping cavity is subjected to a rapid strong pressure pulse, the direction of flow of the liquid from the cavity is determined primarily by the inertial resistance of the liquid displaced. There is more liquid, and thus resistance to flow, on the inlet side than through the nozzle port. The column of liquid that is forced out of the nozzle begins to neck off as a result of surface tension. The stream breaks as the piezoelectric is de-energized, with the remaining column of liquid drawn back into the nozzle. The droplet that has necked off continues its flight with the velocity it achieved in the initial acceleration. Typically, the ejection velocity is about 1–2 meters/sec.

In normal printing applications using 150 micron drops of viscous water-based inks, the head speed is typically about 0.5 meter/sec. This motion adds a transverse velocity component to the droplet trajectory and can affect aiming accuracy. It may also cause the drop to skip when it hits a surface. Droplets fired from a stationary head tend to evaporate more slowly because they follow in the vapor trail of the preceding drop. The heads work most reliably when the inlet supply lines are not required to flex and the liquids are not subjected to acceleration forces.

The size of the drop is determined primarily by the surface tension and by the diameter of the nozzle. The smaller the droplet, the faster it will evaporate and the more its trajectory will be affected by drafts. Nozzles smaller than 25 microns tend to become plugged with dust particles. For water, the drop diameter is approximately 1.5 times the nozzle diameter. Typically drops will not vary in size by more than 5%. We have shown that the jet will also successfully eject a variety of polar solvents including $CH_3CN$ and MeOH. With these less viscous solvents, too forceful an ejection pulse may result in the formation of a series or trailing satellite droplets in addition to the primary drop. The duration of the pulse also affects satelliting.

After the cavity has returned to its original state, a period of time must be allowed for the nozzle to refill by capillary action before another cycle of pulsing can be initiated. It is important for the nozzle refill only to the top of the orifice, but the liquid meniscus not spread out onto the front face of the jet. This is prevented by silanizing the face to reduce its surface tension. The head is also operated under slight negative pressure to prevent overfilling. The aim of the drop is in the axial direction of the nozzle, but defects in the face coating can affect the trajectory.

Arrays of nozzles with up to 64 independent pumping chambers but a common inlet supply have been fabricated. It is important that each chamber inlet have some restriction so that operation of one pumping chamber does not affect the others. The separation between nozzles is typically 400 microns for printing applications, but denser arrays can be produced either by interleaving the transverse motion of the target or decreasing the nozzle spacing. Piezoelectric pumping devices are more thoroughly described in co-pending Application Ser. No. 07/512,957, filed Apr. 23, 1990.

Additional preferred embodiments of the invention will become apparent from the following examples, which are intended to further illustrate the invention, rather than to narrow the scope of the invention.

EXAMPLE 1

Preparation of Array Plates Ready for Oligonucleotide or Peptide Assembly

The hybridization array is synthesized on a glass plate. The plate is first coated with the stable fluorosiloxane 3-(1,1-dihydroperfluoroctyloxy)propyltriethoxysilane. An array of dots is then photoetched onto the coated surface using either an oxygen plasma or medium power $CO_2$ laser to ablate off regions of the fluorosiloxane and expose the underlying silicon dioxide glass. The plate is then coated with glycidyloxypropyl trimethoxysilane, which reacts only on the exposed regions of the glass to form a glycidyl epoxide. The plate is next treated with hexaethyleneglycol and sulfuric acid to convert the glycidyl epoxide into a hydroxyalkyl group, which acts as a linker arm. The hydroxyalkyl group resembles the 5'-hydroxide of nucleotides and provides a stable anchor on which to initiate solid phase synthesis. The hydroxyalkyl linker arm provides an average distance of 3–4 nm between the oligonucleotide and the glass surface. The siloxane linkage to the glass is completely stable to all acidic and basic deblocking conditions typically used in oligonucleotide or peptide synthesis. This scheme for preparing array plates is illustrated in FIG. 2.

EXAMPLE 2

Assembly of Oligonucleotides on the Array Plates

The hydroxyalkylsiloxane surface in the dots has a surface tension of approximately $\gamma=47$, whereas the fluoroxysilane has a surface tension of $\gamma=18$. For oligonucleotide assembly, the solvent of choice is acetonitrile, which has a surface tension of $\gamma=29$. The hydroxyalkylsiloxane surface is thus completely wet by acetonitrile, while the fluorosiloxane masked surface between the dots is very poorly wet by acetonitrile. Droplets of oligonucleotide synthesis reagents in acetonitrile are applied to the dot surfaces and tend to bead up, as shown in FIG. 3. Mixing between adjacent dots is prevented by the very hydrophobic barrier of the mask. The contact angle for acetonitrile at the mask-dot interface is approximately $\theta=43°$. The plate effectively acts as an array microtiter dish, wherein the individual wells are defined by surface tension rather than gravity. The volume of a 40 micron droplet is 33 picoliters. The maximum volume retained by a 50 micron dot is approximately 100 picoliters, or about 3 droplets. A 100 micron dot retains approximately 400 picoliters, or about 12 droplets. At maximum loading, 50 micron and 100 micron dots bind about 0.07 and 0.27 femptomoles oligonucleotide, respectively.

Figure 4:
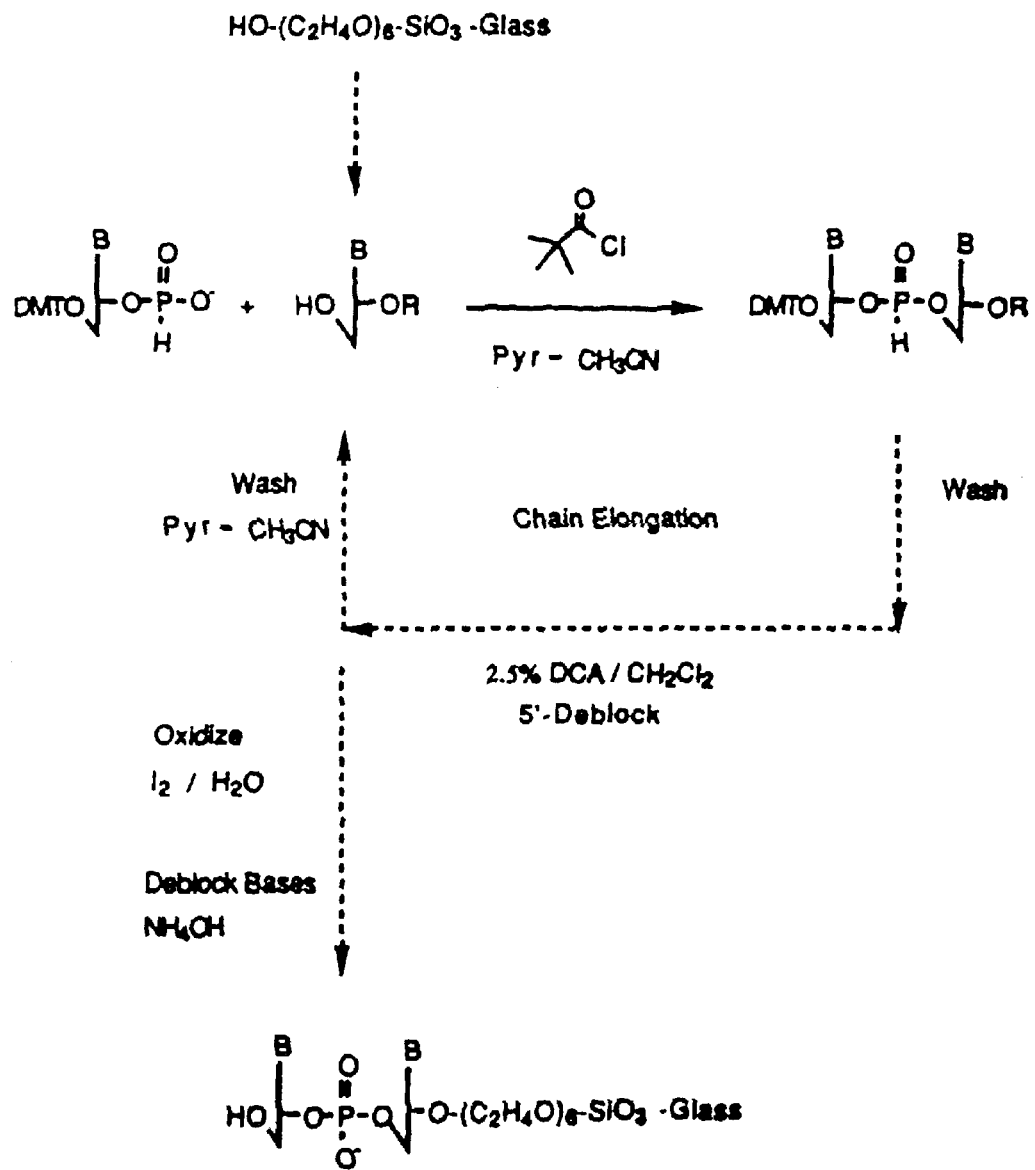
FIG. 4: Hydrogen-phosphonate solid phase oligonucleotide synthesis on an array surface prepared according to Example 1.

Assembly of oligonucleotides on the prepared dots is carried out according to the H-phosphonate procedure, as shown in FIG. 4. Delivery of the appropriate blocked nucleotides and activating agents in acetonitrile is directed to individual dots using the picopump apparatus described in Example 3. All other steps, (e.g., DMT deblocking, washing) are performed on the array in a batch process by flooding the surface with the appropriate reagents. An eight nozzle piezoelectric pump head is used to deliver the blocked nucleotides and activating reagents to the individual dots, and delivering droplets at 1000 Hz, requires only 32 seconds to lay down a 512×512 (262k) array. Since none of the coupling steps have critical time requirements, the difference in reaction time between the first and last droplet applied is insignificant.

EXAMPLE 3

Construction of Piezoelectric Impulse Jet Pump Apparatus

Figure 5:
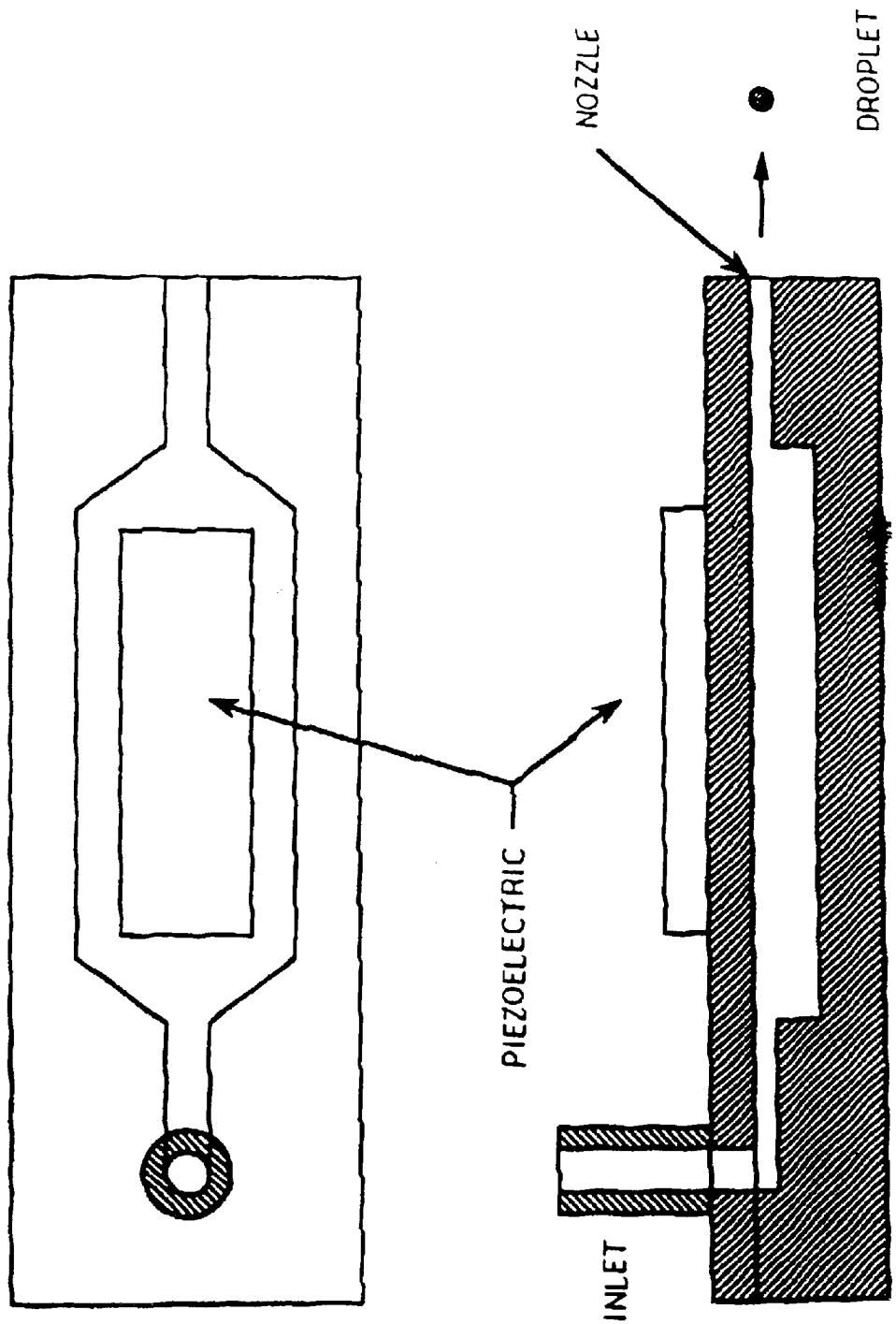
FIG. 5: Top and side views of a piezoelectric impulse jet of the type used to deliver solid phase synthesis reagents to individual dots in the array plate synthesis methods according to the invention.

Piezoelectric impulse jets are fabricated from Photoceram (Corning Glass, Corning, N.Y.), a UV sensitive ceramic, using standard photolithographic techniques to produce the pump details. The ceramic is fired to convert it to a glassy state. The resulting blank is then etched by hydrogen fluoride, which acts faster in exposed then in nonexposed areas. After the cavity and nozzle details are lapped to the appropriate thickness in one plate, the completed chamber is formed by diffusion bonding a second (top) plate to the first plate. The nozzle face is lapped flat and surface treated, then the piezoelectric element is epoxied to the outside of the pumping chamber. When the piezoelectric element is energized it deforms the cavity much like a one-sided bellows, as shown in FIG. 5.

Figure 6:
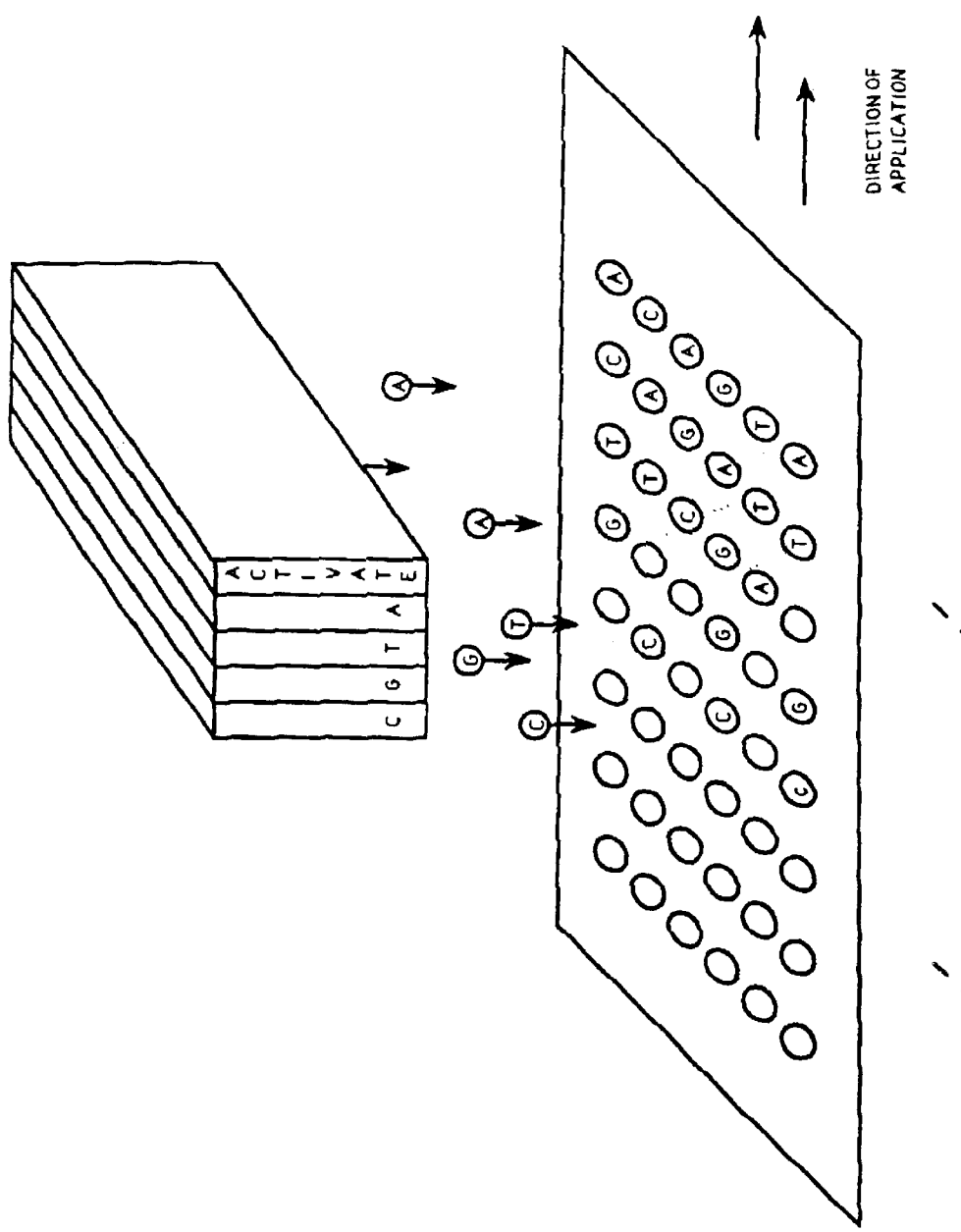
FIG. 6: Use of a piezoelectric impulse jet head to deliver blocked nucleotides and activating agents to individual dots on an array plate. The configuration shown was the stationary head/moving plate apparatus described in Example 3.

To determine the appropriate orifice size for accurate firing of acetonitrile droplets, a jet head with a series of decreasing orifice sizes is Prepared and tested. A 40 micron nozzle produces droplets of about 65 picoliters. A separate nozzle array head is provided for each of the four nucleotides and a fifth head is provided to deliver the activating reagent for coupling. The five heads are stacked together with a mechanically defined spacing. Each head has an array of eight nozzles with a separation of 400 microns. The completed pump unit is assembled with the heads held stationary and the droplets fired downward at a moving array plate as shown in FIG. 6.

Figure 7:
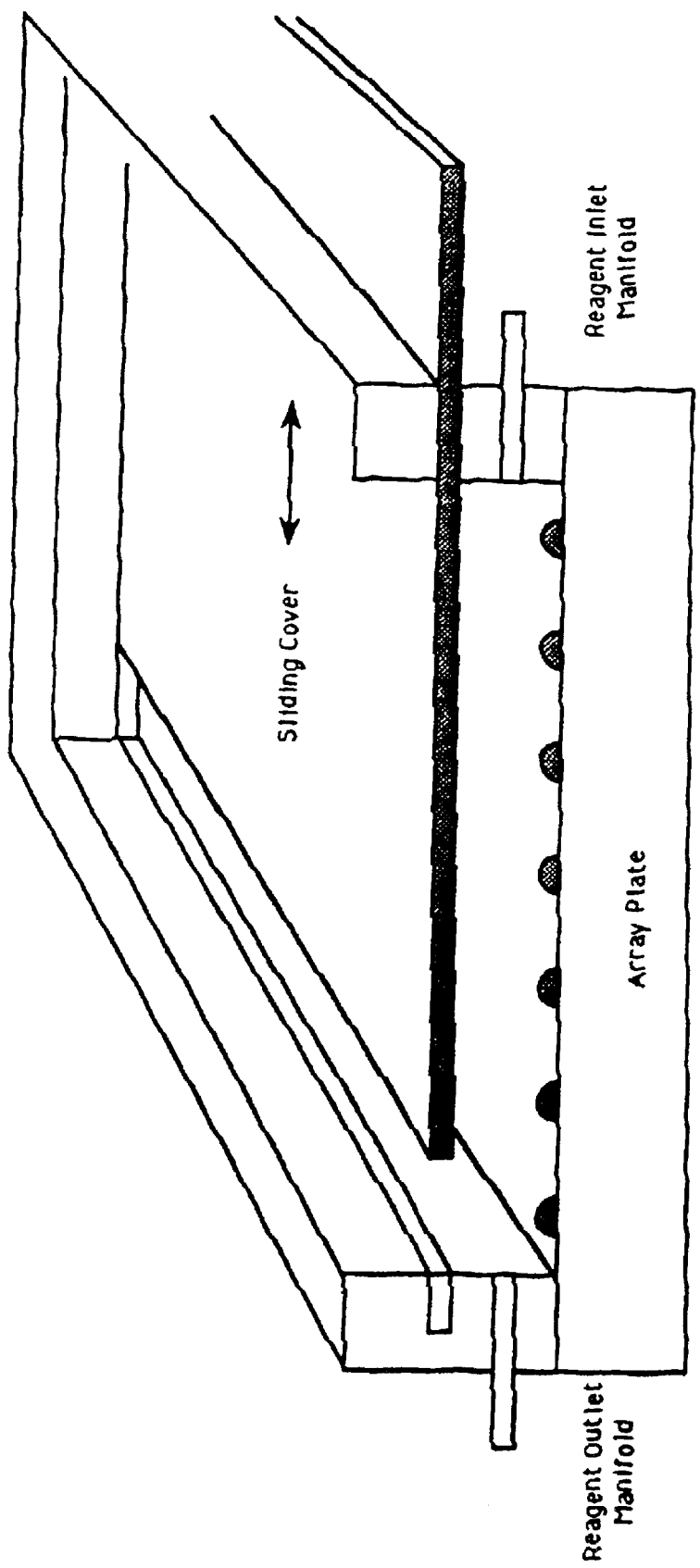
FIG. 7: Enclosure for array reactions, as described in Example 3, showing array plate, sliding cover and manifolds for reagent inlet and outlet.

A plate holding the target array is held in a mechanical stage and is indexed in the X and Y planes beneath the heads by synchronous screw drives. The mechanical stage is similar to those used in small milling machines, microscopes and microtomes, and provides reproducible positioning accuracy better than 2.5 microns or 0.1 mil. As shown in FIG. 7, the plate holder is fitted with a slotted spacer which permits a cover plate to be slid over the array to form an enclosed chamber. Peripheral inlet and outlet ports are provided to allow the plate to be flooded for washing, application of reagents for a common array reaction, or blowing the plate dry for the next dot array application cycle.

Both the stage and head assembly are enclosed in a glove box which can be evacuated or purged with argon to maintain anhydrous conditions. With the plate holder slid out of the way, the inlet lines to the heads can be pressurized for positive displacement priming of the head chambers or flushing with clean solvent. During operation, the reagent vials are maintained at the ambient pressure of the box.

With a six minute chemistry cycle time, the apparatus can produce 10-mer array plates at the rate of 1 plate or $10^6$ oligonucleotides per hour.

EXAMPLE 4

Use of Oligonucleotide Array Plates to Determine the Nucleotide Sequence of a Target Nucleic Acid The oligonucleotide array plate is prepared as described in Examples 1 and 2, using the apparatus described in Example 3. The array contains oligonucleotides having 10 nucleotides each (10-mers). The synthesis is carried out such that each oligonucleotide element, moving in a 5'-3' direction, is identical to the preceding element in nucleotide sequence, except that it deletes the 5'-most nucleotide, and adds a new 3'-most oligonucleotide. In this way the total array represents every possible permutation of the 10-mer oligonucleotide sequence in $4^{10}$ $1.05 \times 10^6$ individual dot elements. Within the oligonucleotide elements oligonucleotides are spaced at 7 nm intervals to provide an oligonucleotide loading density of $3.4 \times 10^{-12}$ moles/cm2, or $2.6 \times 10^{-16}$ moles per 100 micron element. The target nucleic acid is used to probe the oligonucleotide array plate. The probe is labelled with 1000 Ci/mmol $p^{32}$. The labelled probe is contacted with the oligonucleotide array plate for hybridization in a 10 nM solution of probe in 3M $Me_4NCI$ at 42° C. This solution is spread over the oligonucleotide surface to a depth of 160 microns, providing a probe density of $1.6 \times 10^{-13}$ moles/cm$^2$, which is 1/20 of the density of plate-bound oligonucleotide. Turbulent mixing is provided over a distance of 5 oligonucleotide element dot diemeters using sonic agitation. Washes are carried out in 3M $Mc_4NCI$ at 42° C. At 10% hybridization and wash efficiency, each oligonucleotide clement dot having an exact match with the probe binds 26 attomoles of probe. Radiolabel binding is detected using a Bio-Image Analyzer ™ (Fuji, Waltham, MA). The pattern of binding is assessed and the nucleotide sequence of the probe nucleic acid is determined by ordering the nucleotide sequence according to the known sequences of the oligonucleotide elements, as shown in FIG. 1.

What is claimed is:

1. A solid support comprising a support surface with an array of functionalized sites wherein a solution in the amount of about 50 picoliter to 2 microliter at a functionalized site is separated from solutions at other functionalized sites by surface tension, and wherein the support surface of the functionalized site has a higher surface tension relative to the site surface surrounding the functionalized site.

2. The solid support of claim 1 wherein said support surface has 10–10$^4$ functionalized sites per cm$^2$.

3. The solid support of claim 1 wherein said functionalized site is about 50–2000 microns in diameter.

4. The solid support of claim 1 wherein said support surface is glass.

5. The solid support of claim 1 wherein said support surface is selected from the group consisting of nylon, polyethylene, polypropylene, polystyrene and polytetraflourelene.

6. The solid support of claim 1 wherein said functionalized site provides attachment to a nucleic acid.

7. The solid support of claim 1 wherein said functionalized site provides attachment to a peptide.

8. The solid support of claim 1, 6 or 7 wherein said functionalized site provides a covalent attachment.

9. The solid support of claim 1, 6 or 7 wherein said functionalized site provides a non-covalent attachment.

* * * * *

UNITED STATES PATENT AND TRADEMARK OFFICE
CERTIFICATE OF CORRECTION

| | |
|---|---|
| PATENT NO. | : 6,921,636 B1 |
| DATED | : July 26, 2005 |
| INVENTOR(S) | : Brennan |

It is certified that error appears in the above-identified patent and that said Letters Patent is hereby corrected as shown below:

Column 13,
Line 40, delete the first occurrence of "site".

Signed and Sealed this

Twenty-eighth Day of February, 2006

JON W. DUDAS
*Director of the United States Patent and Trademark Office*